United States Patent
Ivey et al.

(10) Patent No.: US 6,375,167 B1
(45) Date of Patent: Apr. 23, 2002

(54) SENSE-SIMILE TRANSMISSION SAMPLER

(75) Inventors: Ellwood G. Ivey, Savannah, GA (US); Greg Beard, Morrisville, NC (US); Michael Horovitz, Savannah, GA (US)

(73) Assignee: Trisenx Holdings, INC, Savannah, GA (US)

( * ) Notice: Subject to any disclaimer, the term of this patent is extended or adjusted under 35 U.S.C. 154(b) by 0 days.

(21) Appl. No.: 09/596,726

(22) Filed: Jun. 16, 2000

Related U.S. Application Data

(63) Continuation-in-part of application No. 09/567,658, filed on May 9, 2000.

(51) Int. Cl.$^7$ .................................................. B01F 3/04
(52) U.S. Cl. ........................ 261/26; 261/30; 261/34.1; 261/42; 261/65; 261/66; 261/82; 261/DIG. 88; 422/124
(58) Field of Search ............................ 261/26, 28, 30, 261/33, 34.1, 42, 65, 66, 81, 82, DIG. 88; 422/123, 124

(56) References Cited

U.S. PATENT DOCUMENTS

| | | | | | |
|---|---|---|---|---|---|
| 5,011,632 | A | * | 4/1991 | Yano et al. | 261/81 |
| 5,318,503 | A | * | 6/1994 | Lord | 600/27 |
| 6,024,783 | A | * | 2/2000 | Budman | 96/222 |

FOREIGN PATENT DOCUMENTS

JP      64-5556    *   1/1989

* cited by examiner

*Primary Examiner*—Robert A. Hopkins
(74) *Attorney, Agent, or Firm*—John L. James

(57) ABSTRACT

A sense-simile sampler delivers a sample fragrance in response to receiving an external signal, preferably via the internet. The sampler has a fragrance reservoir attached to a cylinder via a tube. A piston plunger reciprocates in the cylinder to expel the fragrance. A one-way valve controls flow of fragrance from the reservoir into the cylinder. The piston plunger is solenoid operated via signals from an internet appliance.

9 Claims, 1 Drawing Sheet

SENSE-SIMILE TRANSMISSION SAMPLER

CROSS-REFERENCE TO RELATED APPLICATIONS

This application is a continuation in part of copending application Ser. No. 09/567,658, filed May 9, 2000 by Ellwood G. Ivey, Jr. entitled Sense-Simile Transmission Machine Sampler.

This application is related to copending application Ser. No. 09/252,051, filed Feb. 17, 1999, now U.S. Pat. No. 6,251,032, by Ellwood G. Ivey, Jr. entitled Sense-Simile. Transmission Machine.

This application is related to co-filed application Ser. No. 09/597,732, by Ellwood G. Ivey, Jr. entitled Sense-Simile Transmission Apparatus And Method.

This application is related to co-filed application Ser. No. 09/596,727, by Ellwood G. Ivey, Jr. entitled, Sense-Simile Transmission Sampler.

FIELD OF THE INVENTION

The present invention relates generally to an information transmitting and receiving device, and, more particularly, to a device for delivering sample fragrances.

BACKGROUND OF THE INVENTION

Marketers often use a scratch and sniff insert in printed media to enable a person to smell the aroma of the perfume or other item presented. Smell is easy to add to print media but print media is being replaced by visual media via the internet. Not only does the internet enable us to save trees that would otherwise go to make magazines, but delivers content in color for greater visual appeal. Sound and color are easily available, however, smell has remained more difficult to deliver. Accordingly it will be appreciated that it would be highly desirable to have a device to replicate an aroma that can be used with the internet to complete the transition from a printed magazine with a scratch and sniff insert to a paperless internet with sound and smell.

SUMMARY OF THE INVENTION

Briefly summarized, according to one aspect of the present invention, an apparatus for delivering sample fragrances comprises a cylinder with a sidewall defining an inlet opening, a first end defining an orifice and a second end defining an end opening. A piston plunger is reciprocally mounted in the cylinder to compress the cylinder volume and expel the volume through the orifice. The piston plunger has a rod extending through the end opening that is attached to a solenoid. The solenoid extends the rod in the cylinder to compress the cylinder volume, and retracts the rod to expand the cylinder volume with fragrance from the reservoir. An inlet tube has one end in the reservoir and its other end attached to the sidewall about the inlet opening. The inlet tube delivers fragrance from the reservoir to the cylinder so that the fragrance can be expelled through the orifice with the volume in the cylinder.

A one-way valve in the cylinder permits fluid flow from the reservoir into the cylinder and prevents fluid flow from the cylinder into the reservoir. The one-way valve opens as the piston rod retracts to fill the cylinder with fragrance, and it closes as the piston rod extends to expel the cylinder volume, including the fragrance, through the jet orifice.

The apparatus can be connected to a computer or other internet appliance via a serial port so that when a particular internet web site is visited the fragrance can be released. A battery contained in a housing with the apparatus supplies energy for solenoid operation. An electronic switch interposed between the battery and the solenoids responds to an external signal via the serial port to selectively power the solenoids. The external signal can come via the internet when a particular web site is visited and a fragrance sample is requested by clicking on a fragrance icon.

These and other aspects, objects, features and advantages of the present invention will be more clearly understood and appreciated from a review of the following detailed description of the preferred embodiments and appended claims, and by reference to the accompanying drawings.

DETAILED DESCRIPTION OF THE PREFERRED EMBODIMENT

The present invention is a sampler for a sensualizer or sense-simile machine. A sense-simile machine facilitates the virtual transmission of flavors, smells, material textures and environmental conditions from one location to another over a standard communications link, such as a telephone line, for example. At the transmitting end of the line, the user inputs data representative of the sense information to be transmitted. For example, a restaurant may want to communicate the smell and taste of a particular item. The restaurant inputs information pertaining to the smell and flavor of the item according to predetermined parameters for the particular smell or flavor. This is easily done via a computer program once the smells and flavors have been identified and quantified. The restaurant transmits the code which arrives at the receiver into a receiving unit that deciphers the code and causes the machine to emit the corresponding odor and the corresponding flavor or other conditions that have been transmitted. When used for internet shopping, a receiving unit is connected to a computer which accesses a particular merchant. In the case of a restaurant, its web site will contain pictures of various food icons along with their sense-simile codes. A transmission occurs when the particular food item is clicked on the screen or the coded information is input via the computer keyboard to activate the sense-simile machine to produce the aroma and taste connected with the food. The present sampler continues the transition from print media to the internet by essentially providing the internet equivalent of a scratch and sniff magazine insert.

Figure 1:
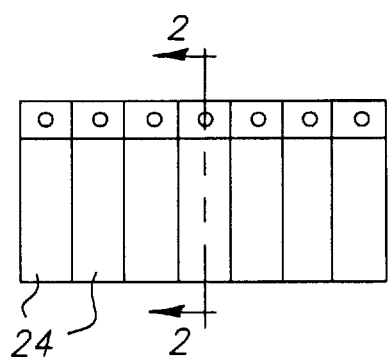
FIG. 1 is a front view of a preferred embodiment of a sense-simile sampler for multiple fragrance samples which fragrance incorporates reservoirs and piston plungers according to the present invention.
Figure 2:
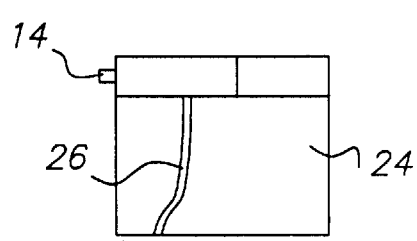
FIG. 2 is a sectional side view taken along line 2—2 of FIG. 1.
Figure 3:
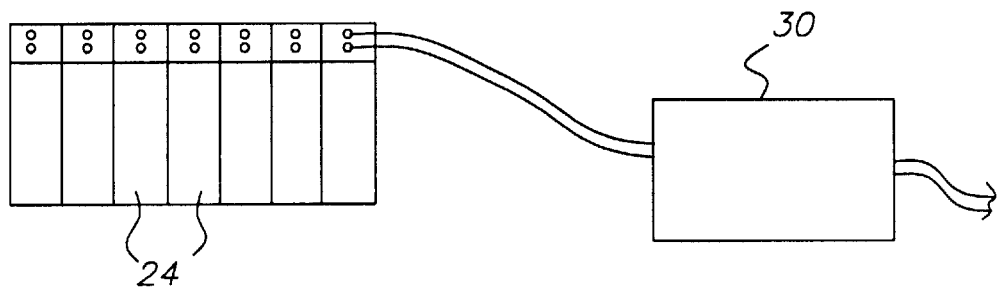
FIG. 3 is a rear view of the sampler of FIG. 1.
Figure 4:
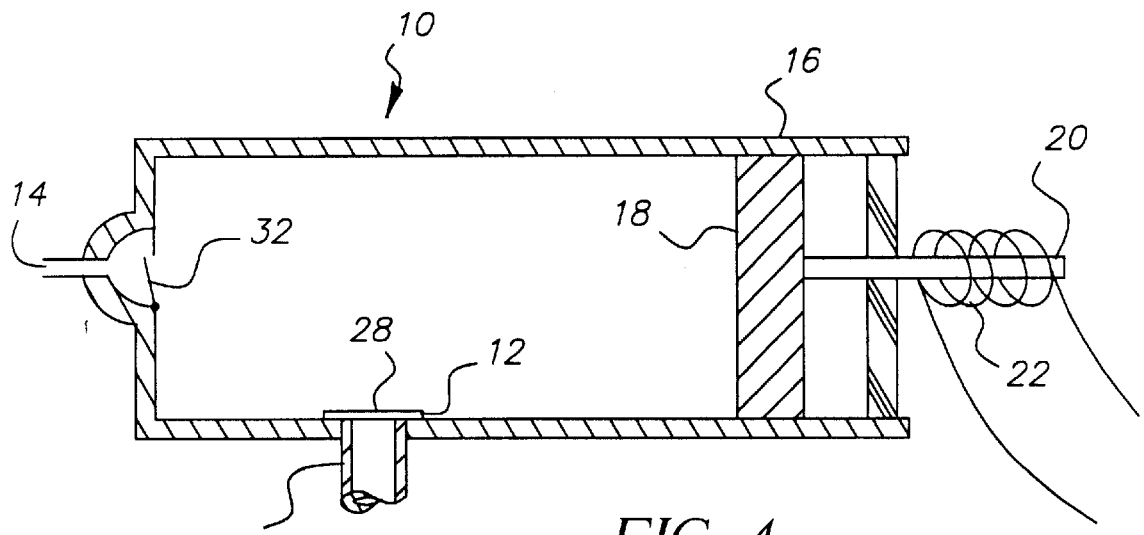
FIG. 4 is a somewhat enlarged sectional side view of the piston plunger of FIG. 2.

Referring to FIG. 1, a cylinder 10 has a sidewall defining an inlet opening 12, a first end defining an orifice 14 and a second end 16 defining an end opening. A piston plunger 18 is reciprocally mounted in the cylinder 10. The piston plunger 18 has a rod 20 extending through the end opening. A solenoid 22 is attached to the rod to operate the piston plunger. The rod extends in the cylinder to compress the volume in the cylinder thereby forcing the volume through jet orifice 14. The solenoid 22 retracts rod 20 to restore the volume of the cylinder.

The cylinder 10 is connected to a fragrance reservoir 24 via a tube 26. Inlet tube 26 has one end that extends into the reservoir 24 and has its other end attached to the cylinder about the inlet opening 12 in the sidewall. Inlet tube 26 delivers fragrance from the reservoir to the cylinder to be forced through the orifice with the cylinder volume.

A one-way valve 28 in one of the cylinder, reservoir and inlet tube permits fluid flow through the inlet tube 26 in only one direction. Fluid flows from the reservoir into the cylinder so that fragrance is available in the cylinder when the piston rod extends to compress the cylinder volume and expel the volume through the jet orifice. Preferably, the one-way valve is a flap attached inside the sidewall adjacent the inlet opening. The flap closes covering the inlet opening as the piston rod extends and the flap opens uncovering the inlet opening as the rod retracts.

A second one-way valve 32 in the jet nozzle end of the cylinder permits fluid flow from the cylinder through the jet orifice 14 but prevents fluid flow in the opposite direction to prevent diluting the fragrance in the cylinder ready for expulsion.

The solenoid 22 can be controlled from a computer or internet appliance using the serial port. Solenoid 22 is operated by a control circuit 30 which preferably includes a battery. Control circuit may contain the equivalent of an electronic ladder switch which routes the incoming signal to one of the solenoids according to the strength or other characteristic of the incoming signal. The control circuit is activated from an internet appliance by clicking on a screen icon. As illustrated there are seven reservoirs, each with a solenoid, to allow sampling seven fragrances, either different fragrances or the same fragrance. When a particular fragrance is chosen, its icon is clicked to activate the control circuit and its associated solenoid.

It can now be appreciated that a sense-simile machine sampler has been presented that allows a person to sample a fragrance, such as a perfume. The present invention literally replaces sniff and scratch technology commonly used for fragrance samples in magazines and other print media. The sampler can be refilled with fragrance and used repeatedly. The sampler is activated by accessing the internet web page of the company distributing the sampler and clicking icons as directed.

While the invention has been described with particular reference to the preferred embodiments, it will be understood by those skilled in the art that various changes may be made and equivalents may be substituted for elements of the preferred embodiments without departing from invention. For example, it is possible to employ circuitry other than that illustrated and described, or to employ different circuit components from those described. It is accordingly intended that the claims shall cover all such modifications and applications as do not depart from the true spirit and scope of the invention.

What is claimed is:

1. An apparatus, comprising:

a cylinder having a sidewall defining inlet opening, a first end defining an orifice and a second end defining an end opening;

a piston plunger reciprocally mounted in said cylinder, said piston plunger having a rod extending through said end opening;

a solenoid attached to said rod to operate said piston, said rod extending to compress volume in said cylinder forcing said volume through said orifice, said piston retracting to restore volume of said cylinder;

a reservoir; and an inlet tube having one end in said reservoir and its other end attached to said sidewall about said inlet opening, said inlet tube delivering fragrance from said reservoir to said cylinder, said fragrance being forced through said orifice with said volume.

2. An apparatus, as set forth in claim 1, including a one-way valve in one of said cylinder, reservoir and inlet tube to permit fluid flow from said reservoir into said cylinder and preventing fluid flow from said cylinder into said reservoir.

3. An apparatus, as set forth in claim 2, wherein said one-way valve comprises a flap attached inside said sidewall adjacent said inlet opening.

4. An apparatus, as set forth in claim 3, wherein said flap closes covering said inlet opening as said piston rod extends and said flap opens uncovering said inlet opening as said rod retracts.

5. An apparatus, as set forth in claim 1, wherein said solenoid is controlled from an internet appliance.

6. An apparatus, as set forth in claim 1, wherein there are several reservoirs.

7. An apparatus, as set forth in claim 1, including a one-way valve in said cylinder to permit fluid flow from said cylinder through said orifice and prevent fluid flow into said cylinder through said orifice.

8. An apparatus, as set forth in claim 7, wherein said one-way valve comprises a flap attached to said cylinder adjacent said orifice.

9. An apparatus, as set forth in claim 8, wherein said flap closes blocking said orifice opening as said piston rod retracts and said flap opens unblocking said orifice as said rod extends.

* * * * *